United States Patent
Ishikawa

(10) Patent No.: US 6,892,564 B2
(45) Date of Patent: May 17, 2005

(54) FALL IMPACT APPARATUS

(75) Inventor: Katsumi Ishikawa, Tokyo (JP)

(73) Assignee: Uniden Corporation, Tokyo (JP)

( * ) Notice: Subject to any disclaimer, the term of this patent is extended or adjusted under 35 U.S.C. 154(b) by 0 days.

(21) Appl. No.: 10/744,528

(22) Filed: Dec. 23, 2003

(65) Prior Publication Data

US 2005/0016256 A1 Jan. 27, 2005

(30) Foreign Application Priority Data

Jul. 7, 2003 (JP) ........................................ 2003-271295

(51) Int. Cl.$^7$ .............................................. G01N 3/30
(52) U.S. Cl. ..................................................... 73/12.06
(58) Field of Search ............................ 73/12.01, 12.04, 73/12.06, 12.09, 12.13

(56) References Cited

U.S. PATENT DOCUMENTS

| | | | | |
|---|---|---|---|---|
| 4,640,120 A | * | 2/1987 | Garritano et al. | 73/12.13 |
| 5,824,880 A | * | 10/1998 | Burwell et al. | 73/12.06 |
| 6,508,103 B1 | * | 1/2003 | Shim et al. | 73/12.05 |
| 6,604,413 B2 | * | 8/2003 | Panek et al. | 73/119 A |

FOREIGN PATENT DOCUMENTS

| | | |
|---|---|---|
| JP | U 56-138347 | 10/1981 |
| JP | 2000-055778 | 2/2000 |
| JP | 2000-065677 | 3/2000 |

* cited by examiner

Primary Examiner—Max Noori
(74) Attorney, Agent, or Firm—Steven J. Hutlquist; Marianne Fuierer; Yongzhi Yang

(57) ABSTRACT

An object of the present invention is to provide a fall impact apparatus, namely a fall impact apparatus, which is capable of fixing the attitudinal angle of a test subject during a drop test until the moment at which the test subject collides with a dropping subject surface.

The fall impact apparatus includes a test subject fixing member for fixing a test subject which is to be tested for impact strength at a desired attitudinal angle, a hoisting and dropping member for raising and dropping the test subject fixing member to which the test subject is fixed along the falling direction of the test subject, and a dropping subject surface structured so as to collide only with the test subject at the terminal end of the falling direction without interfering with the hoisting and dropping member when the hoisting and dropping member is dropped together with the test subject fixing member. The test subject fixing member is supported by the hoisting and dropping member without being affixed thereto such that when the test subject collides with the dropping subject surface, the fixing member separates freely from the hoisting and dropping member.

4 Claims, 6 Drawing Sheets

FALL IMPACT APPARATUS

BACKGROUND OF THE INVENTION

1. Field of the Invention

The present invention relates to a drop testing device, namely a fall impact apparatus, for testing the tolerance of a product against free fall impact.

2. Description of the Related Art

Portable electronic devices such as portable telephones, MD players, and electronic dictionaries have conventionally been tested for impact resistance using a fall impact apparatus in order to improve the reliability of such products.

In such fall impact apparatus, the test subject must be dropped in a free fall manner or as close to such free fall conditions as possible. When caused to free fall from a sufficiently high position, however, the test subject rotates during the free fall, and thus the site which collides with the surface cannot be kept constant. As a result, test results cannot be reproduced repeatedly.

In order to solve this problem, a fall impact apparatus using a hand-like shaped apparatus which is capable of releasably grasping the test subject is disclosed in Japanese Patent Application Laid-Open No. 2000-55778. This device comprises a position detection means for detecting that the test subject has fallen to a height at which the test subject is to be released from by the grasping of the hand-like shaped apparatus, and thus the test subject is released with good timing just before impact. By means of this construction, the attitudinal angle of the test subject is maintained until the moment of release.

Further, a method of dropping a test subject wherein the test subject is hung by a cord-form material is disclosed in Japanese Patent Application Publication Laid-Open No. 2000-65677. In this device, the test subject is held by the cord-form material until the moment of impact with a base.

However, in the aforementioned fall impact apparatus which comprises the hand-like shaped apparatus, the test subject falls freely for a short period of time following release from the apparatus, and thus change may occur in the attitudinal angle of the test subject. Moreover, a position detection means and a means for automatically releasing the test subject have to be provided, which tends to complicate the structure of the device.

In the dropping device which holds the test subject by a cord-form material, the cord-form material itself may swing or vibrate during the dropping process due to air resistance or the like, and hence the attitude of the test subject cannot be sufficiently maintained as the attitude originally set prior to starting the free fall action.

It is therefore an object of the present invention to provide a fall impact apparatus which is capable of fixing the attitudinal angle of a test subject during a drop test by free fall until the moment of impact with an impact surface.

SUMMARY OF THE INVENTION

In order to achieve the object described above, a fall impact apparatus according to the present invention comprises a test subject fixing member for fixing a test subject which is to be tested for impact strength at a desired attitudinal angle, a hoisting and dropping member for raising and along the falling direction of the test subject, dropping the test subject fixing member to which the test subject is fixed, and a dropping subject surface structured so as to collide only with the test subject at the terminal end of the falling direction without interference of the hoisting and dropping member when the hoisting and dropping member is dropped together with the test subject fixing member. The test subject fixing member is supported by the hoisting and dropping member without being affixed thereto such that when the test subject collides with the dropping subject surface, the fixing member separates freely from the hoisting and dropping member.

According to this construction, the test subject can be fixed at any desired attitudinal angle prior to the start of the drop test, and this attitudinal angle can be maintained until the moment of impact with the dropping subject surface. Since control can be performed such that a desired site of the test subject collides with the dropping subject surface at a desired angle, drop test results can be reproduced repeatedly.

Furthermore, the test subject fixing member is supported by the hoisting and dropping member without being affixed thereto, and therefore separates from the hoisting and dropping member without resistance as the test subject collides with the dropping subject surface. As a result, effects thereof on the drop test values can be prevented.

Here, "supported without being affixed" means that the test subject fixing member and the hoisting and dropping member are not fixed to each other in a manner which would affect the drop test values. For example, the two members are not fixed together using adhesion means such as an adhesive or adhesive tape, and thus upon impact the test subject fixing member separates from the hoisting and dropping member easily, without resistance, and without receiving force therefrom. In other words, "supported without being affixed" corresponds to a state in which drop test results that can be considered substantially identical to a case in which the test subject falls independently and freely can be obtained.

The fall impact apparatus is preferably constructed such that the hoisting and dropping member is formed by a frame body having a through hole through which the dropping subject surface passes the frame body through, the fixing member is placed on this frame body, and at the terminal end of the falling direction, the dropping subject surface passes through the through hole such that when the test subject collides with the dropping subject surface, the fixing member separates from the frame body.

According to this construction, the dropping subject surface passes through the through hole when the hoisting and dropping member is dropped, and the hoisting and dropping member itself falls further downward without colliding with the dropping subject surface. At this time, the test subject is placed across the through hole of the hoisting and dropping member, and thus it is possible to cause only the test subject to collide with the surface.

It is further preferable that the fall impact apparatus comprises an attitude adjusting table provided directly beneath the hoisting and dropping member and capable of moving in a direction which closes the through hole and a direction which opens the through hole.

According to this construction, when the test subject is to be fixed to the test subject fixing member, the attitude adjusting table is moved so as to close the through hole. Thus the test subject can be placed on the attitude adjusting table and adjusted to a desired attitude in a stable situation. When a drop test is to be performed, the attitude adjusting table is moved so as to open the through hole.

According to the fall impact apparatus of the present invention as described above, the attitudinal angle of the test subject can be fixed and maintained by the test subject fixing member until the moment of impact with the dropping subject surface, and thus drop test results can be reproduced repeatedly. Moreover, the test subject fixing member separates from the hoisting and dropping member as the test subject collides with the dropping subject surface, and thus drop test results that can be considered substantially identical to a case in which a test subject is dropped independently and freely can be obtained.

DESCRIPTION OF THE PREFERRED EMBODIMENTS

Preferred embodiments of the present invention will be described below with reference to the drawings. Note that the embodiments described below are examples to illustrate the present invention, and the present invention is not limited to or by these embodiments.

Figure 1:
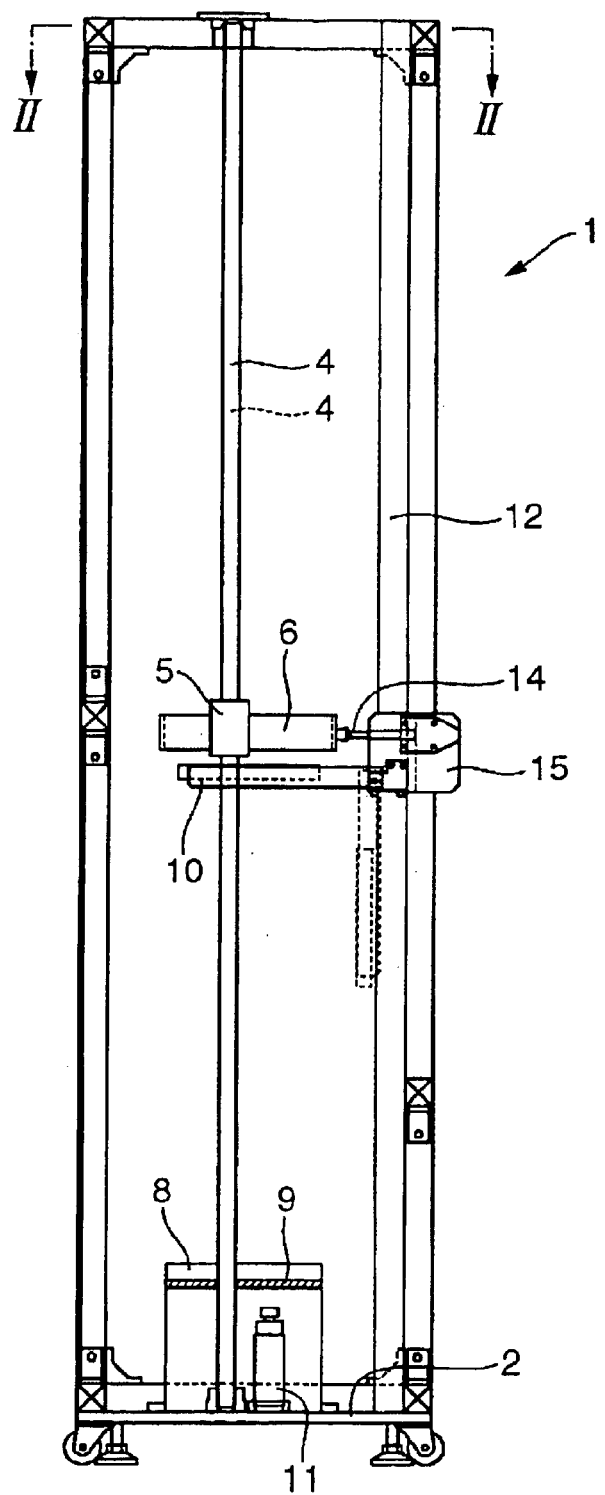
FIG. 1 is a side view of a fall impact apparatus prior to the setting of a test subject and a test subject fixing member.
Figure 2:
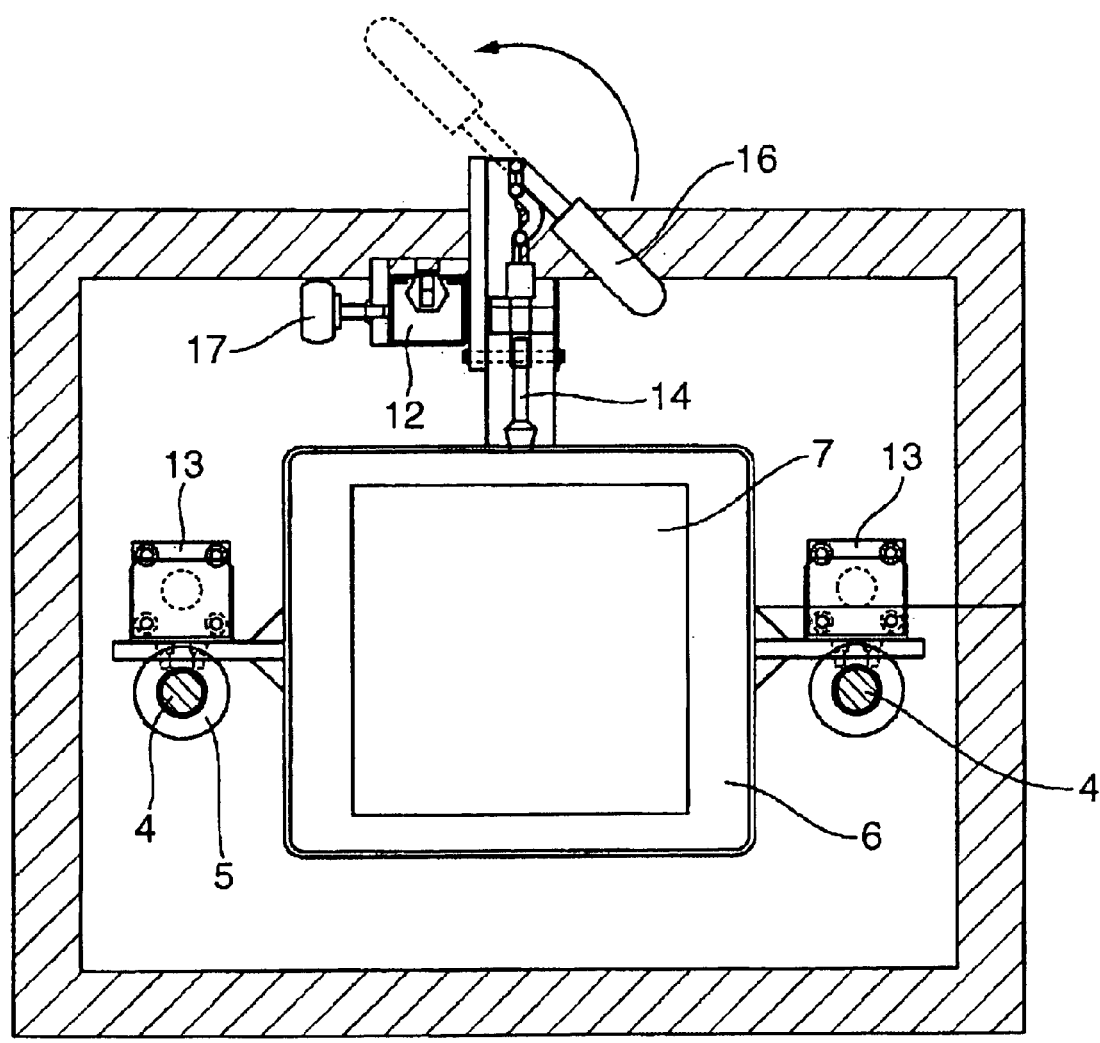
FIG. 2 is a cross-sectional view along the II—II line in FIG. 1.
Figure 3:
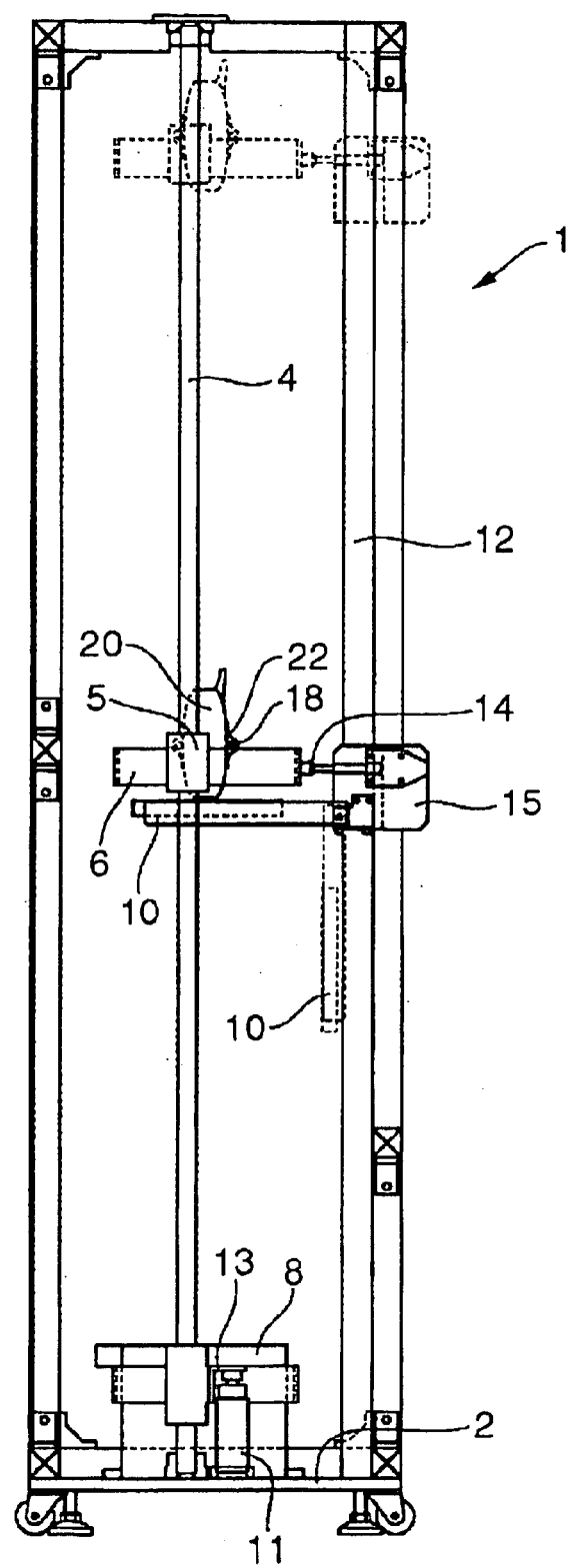
FIG. 3 is a side view of the test device following the setting of the test subject and test subject fixing member.
Figure 4:
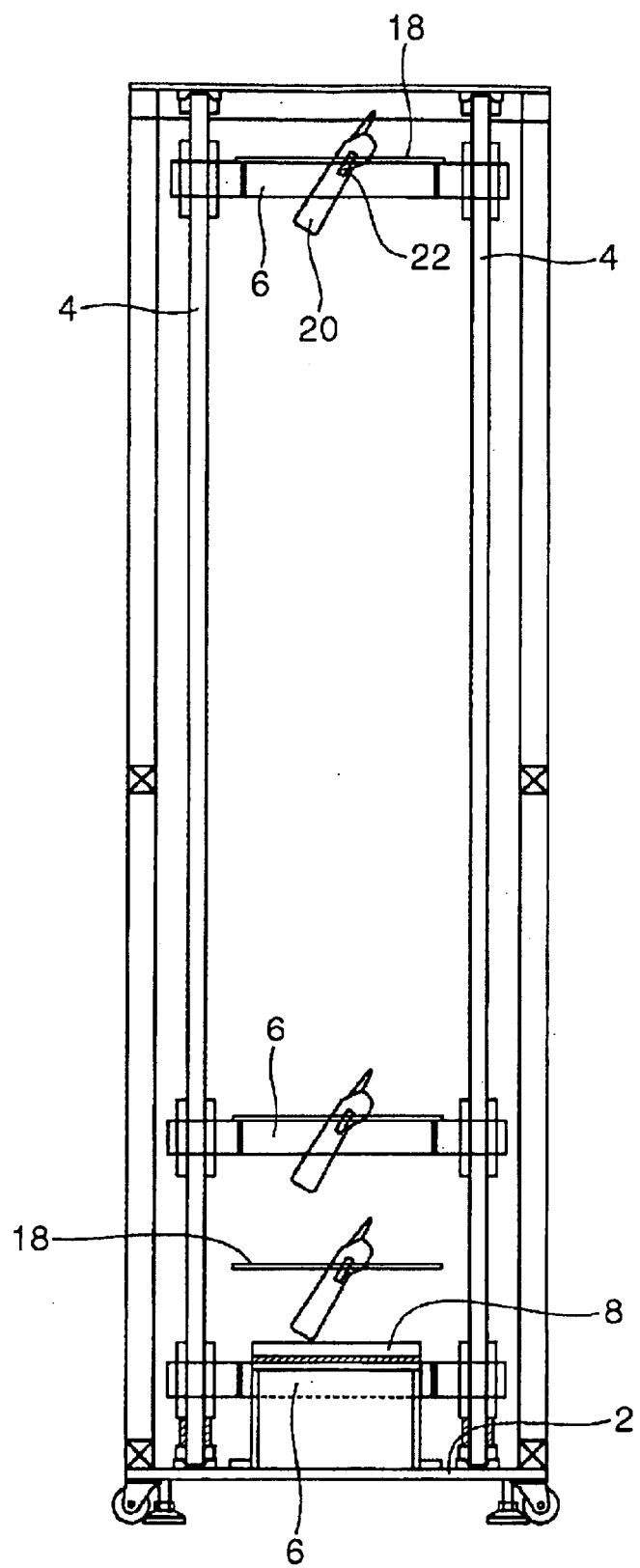
FIG. 4 is a front view of the test device for illustrating the situation in which a drop test is implemented.
Figure 5:
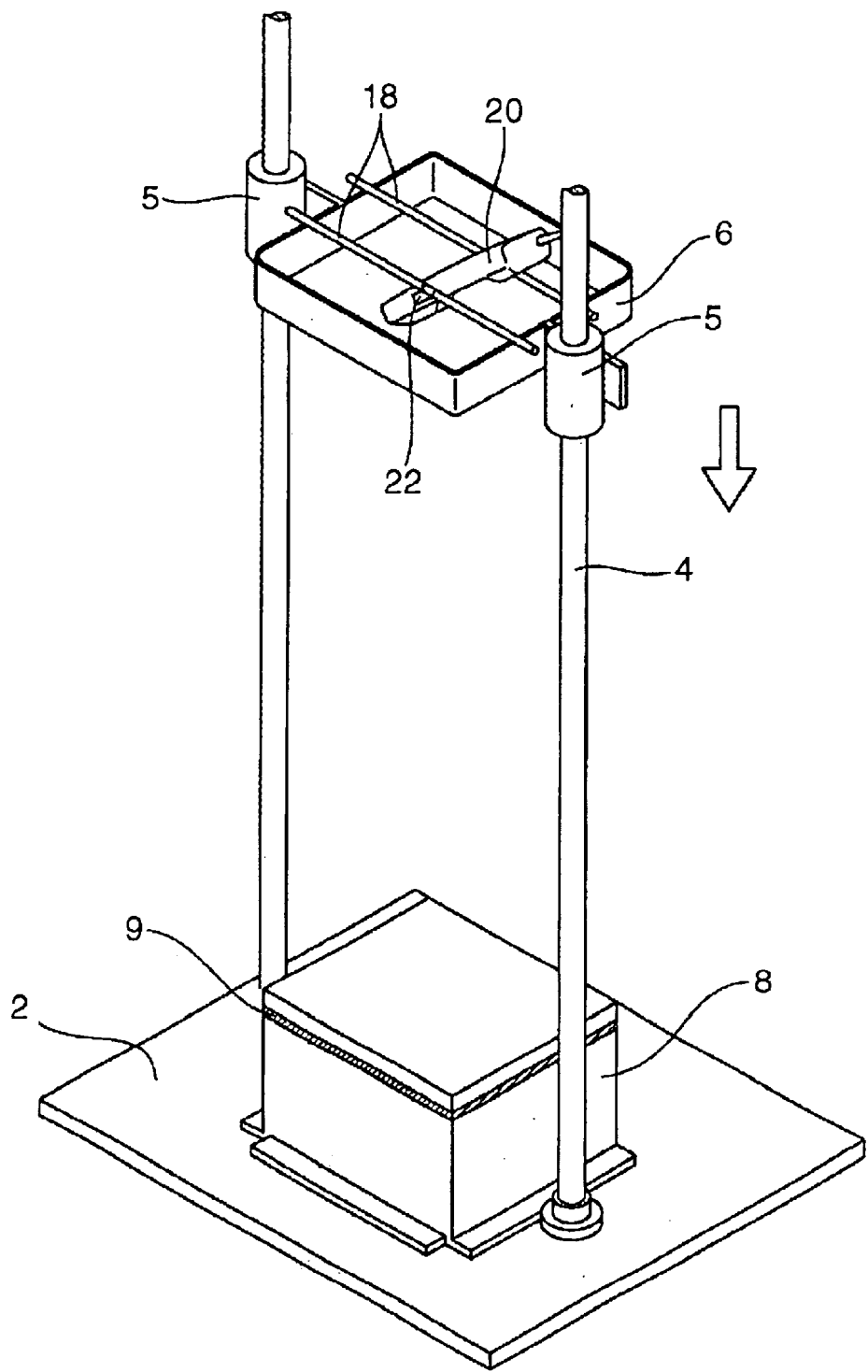
FIG. 5 is a partial perspective view of the test device showing the test subject as it drops.
Figure 6:
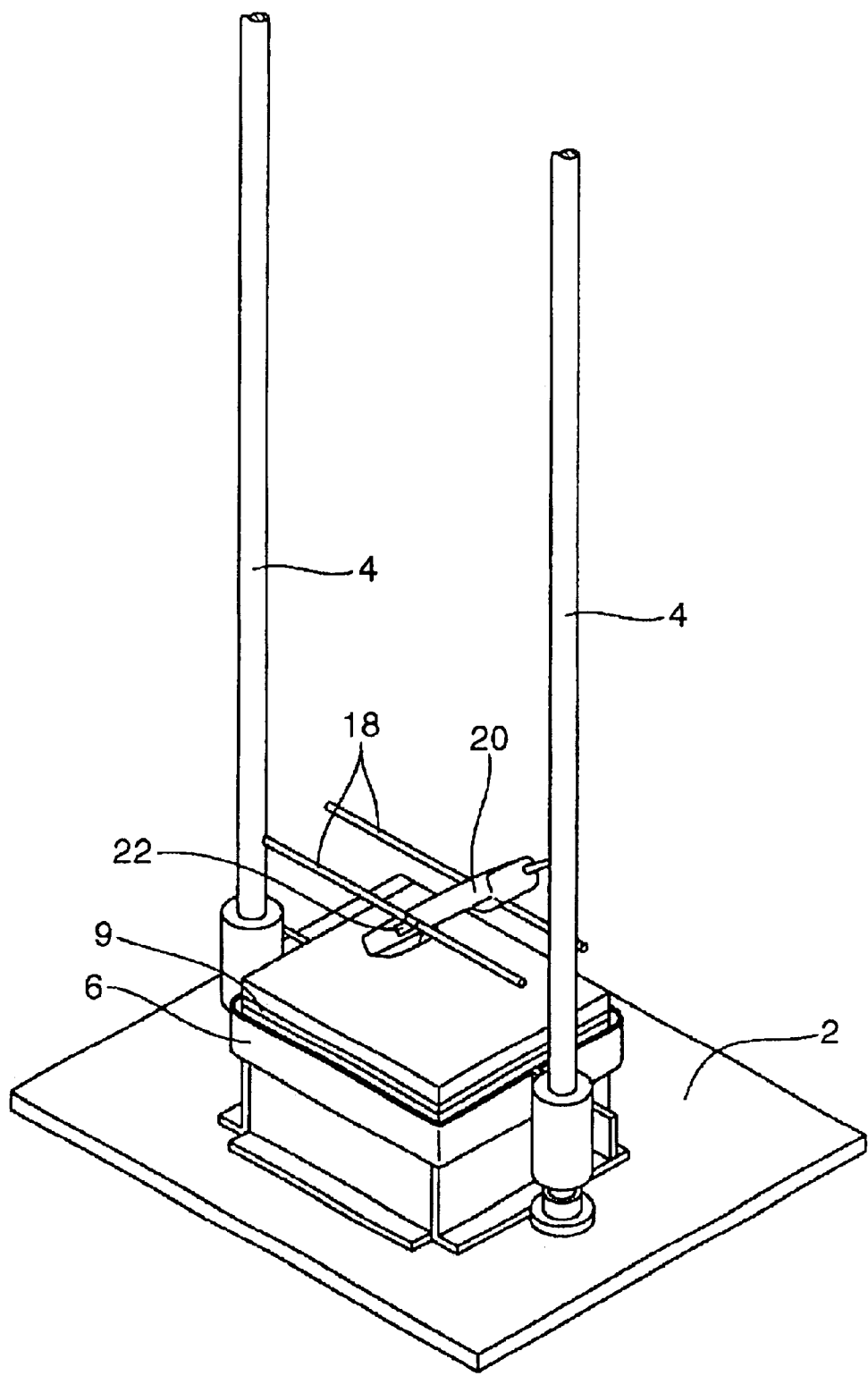
FIG. 6 is a partial perspective view of the test device showing the test subject having collided with the surface.

FIG. 1 is a side view of a fall impact apparatus prior to the setting of a test subject and a test subject fixing member, FIG. 2 is a plan view showing a hoisting and dropping member and a stopper mechanism, FIG. 3 is a side view of the test device following the setting of the test subject and test subject fixing member, FIG. 4 is a front view of the test device for illustrating the situation in which a drop test is implemented, FIG. 5 is a partial perspective view of the test device showing the test subject as it drops, and FIG. 6 is a partial perspective view of the test device showing the test subject having collided with the surface.

First, referring to FIGS. 5 and 6, the schematic construction of the fall impact apparatus will be described. A portable telephone 20 is used as the test subject. A test subject fixing member is constituted by two sticks of split bamboo 18, and this is fixed to the portable telephone 20 by adhesive tape 22 to set the portable telephone 20 at the desired attitudinal angle. The two sticks of split bamboo 18 are placed across a frame-form hoisting and dropping member 6, and the hoisting and dropping member 6 is dropped in the direction of the arrow (see FIG. 5). A dropping subject surface 8 is provided at the terminal end of the falling direction of the hoisting and dropping member, and the portable telephone 20 collides with the dropping subject surface 8. At this time, the hoisting and dropping member 6 does not collide with the surface 8, but bypasses the surface 8 and continues to drop. Since the split bamboo sticks 18 and hoisting and dropping member 6 are not adhered to each other, the split bamboo sticks 18 are easily separated from the hoisting and dropping member 6 at the moment of impact. Hence a state in which the portable telephone 20 falls independently can be accurately reproduced (FIG. 6).

Next, referring to FIGS. 1 through 4, the fall impact apparatus 1 will be described in detail. As shown in the side view of FIG. 1 and the plan view of FIG. 2, two guides 4 and a support post 12 are provided in a vertical direction on a base 2 of the fall impact apparatus 1. A tubular member 5 is fixed to each side of the hoisting and dropping member 6, and the two guides 4 pass through the interior of the respective tubular members 5. Thus the hoisting and dropping member 6 is guided by the guides 4 so as to be capable of rising and falling freely.

As shown in FIG. 2, the hoisting and dropping member 6 is formed by a frame body having a substantially square through hole 7 on the inside thereof. The dropping subject surface 8 is provided directly below the through hole 7 of the hoisting and dropping member 6 in a shape having a slightly smaller surface area than the through hole 7. Cushioning material 9 is inserted into the dropping subject surface 8 parallel to the base 2. Plate-form protruding portions 13 are attached to both sides of the hoisting and dropping member 6. Shock absorbing members 11 are provided on the base 2 in the positions to which the protruding portions 13 fall so that the hoisting and dropping member 6 does not collide directly with the base 2.

An attitude adjusting table 10 is foldably attached to the support post 12 via a movable member 15. By moving the attitude adjusting table 10 to a position in which the through hole 7 is closed (the position indicated in the drawings by the solid line), the portable telephone 20 can be placed on the attitude adjusting table 10, and thus the portable telephone 20 can be set in a desired attitudinal angle with respect to the split bamboo sticks 18. When the portable telephone 20 is to be dropped, the attitude adjusting table 10 is folded into a position in which the through hole is opened (the position shown in the drawings by the dotted line).

Note that the movable member 15 is fixed to the support post 12 by a clamp 17 (a fixing means). By loosening a screw (a fastening means) of the clamp 17, the movable member 15 can be moved up and down along the support post 12, and by tightening the screw at a desired height, the movable member 15 can be fixed.

A stopper 14 is also attached to the movable member 15 to hold the hoisting and dropping member 6 in position and prevent the hoisting and dropping member 6 from falling. The stopper 14 will be described with reference to FIG. 2. When a lever 16 is in a position indicated by the solid line, the stopper 14 is inserted into a hole provided on a side face of the hoisting and dropping member 6, thereby holding in position the hoisting and dropping member 6 to prevent the hoisting and dropping member 6 from falling. When the lever 16 is moved to a release position indicated by the dotted line, the stopper 14 is removed from the hole in the hoisting and dropping member 6 and the hoisting and dropping member 6 falls down along the guides 4.

As shown in FIGS. 3 through 6, the split bamboo sticks 18 are used as a test subject fixing member in this embodiment. The split bamboo sticks 18 are longer than each edge of the hoisting and dropping member 6 and are laid across the hoisting and dropping member without being fixed thereto. The test subject is fixed to the split bamboo sticks 18 by adhesive tape or the like so as to be placed in a desired attitude when the split bamboo sticks 18 are laid across the hoisting and dropping member 6.

Next, an operation of the fall impact apparatus 1 according to this embodiment will be described using an example in which the portable telephone 20 is used as a test subject.

First, as shown in FIG. 3, the clamp 17 is fixed at a height at which the movable member 15 can be operated easily, and the attitude adjusting table 10 is set in the position shown by the solid line, or in other words a position at which the through hole 7 is closed. The attitude of the portable telephone 20 is then set such that the site which is to collide with the dropping subject surface becomes the lower end thereof. In order to maintain this attitude, the portable telephone 20 is positioned between the two split bamboo sticks 18 laid across the hoisting and dropping member 6 and fixed to the split bamboo sticks 18 with adhesive tape 22. Next, the attitude adjusting table 10 is folded into the position shown by the dotted line such that the through hole in the hoisting and dropping member 6 is opened, and then the screw of the clamp 17 is loosened to move the movable member 15 to a drop starting position (the position shown in FIG. 3 by the dotted line). The lever 16 is then rotated (see FIG. 2), whereby the stopper 14 is released and the portable telephone begins to fall.

As shown in FIGS. 4 and 5, the hoisting and dropping member 6 falls along the two guides 4 together with the split bamboo sticks to which the portable telephone 20 is fixed. A bearing or the like is provided between each interior of the tubular member 5 and the surface of the guides 4, and the bearing or the like is processed so that friction is not generated. As a result, the hoisting and dropping member 6 can fall along the guides 4 as in a free falling motion. The portable telephone 20 falls while fixed at an attitudinal angle adjusted using the attitude adjusting table and collides with the dropping subject surface 8. Note that in FIGS. 4 and 5, the support post 12, movable member 15, stopper 14, attitude adjusting table 10, and other elements are not illustrated.

The split bamboo sticks 18 which are merely laid across the hoisting and dropping member 6 disengage from the hoisting and dropping member 6 easily as the portable telephone 20 collides with the dropping subject surface 8. The mass of the split bamboo sticks 18 is negligible compared to the mass of the portable telephone 20, and thus upon impact almost no gravitational force beyond the weight of the portable telephone 20 itself bears upon the portable telephone 20. Hence it is possible to substantially reproduce drop test conditions similar to a case in which the portable telephone 20 is dropped independently.

Meanwhile, the horizontal section of the through hole in the hoisting and dropping member 6 is larger than the horizontal section of the dropping subject surface 8, and thus the hoisting and dropping member 6 does not collide with the dropping subject surface 8 but continues to fall below the upper face of the dropping subject surface 8. The hoisting and dropping member 6 stops falling when the protruding portions 13 collide with the shock absorbing members 11. By providing the shock absorbing members 11, the hoisting and dropping member 6 can be prevented from colliding directly with the dropping subject surface 8, and as a result the durability of the fall impact apparatus can be improved.

In fall impact apparatus, the shock upon impact often differs according to the material or hardness of the surface on which the device is placed. In the fall impact apparatus 1 according to this embodiment, however, the cushioning material 9 is inserted into the dropping subject surface 8, thereby absorbing the effect of the surface on which the device is placed, and thus test results can be reproduced repeatedly even when the test implementation location is altered.

What is claimed is:

1. A fall impact apparatus testing for fall impact resistance of a test subject, said apparatus comprising:

a test subject fixing member for positioning and fixing said test subject at a desired attitudinal angle to said fixing member;

a hoisting and dropping member hoisting said test subject fixing member, supporting said test subject member, and dropping together with said test subject fixing member along the free falling direction of said test subject; and a surface being impacted with the said test subject, said surface being formed so as to collide only with said test subject at the terminal end of the falling direction without interfering with said hoisting and dropping member when said hoisting and dropping member is dropped together with said test subject fixing member, wherein said test subject fixing member is supported by said hoisting and dropping member without being affixed thereto such that when said test subject collides with said surface, said fixing member separates freely from said hoisting and dropping member.

2. The fall impact apparatus according to claim 1, wherein said hoisting and dropping member is comprised of a frame body formed by a through hole through which said surface passes the frame body, said fixing member is placed on this frame body, and at the terminal end of said falling direction, said dropping subject surface passes through said through hole such that when said test subject and said surface collide, said fixing member separates from said frame body.

3. The fall impact apparatus according to claim 1, further comprising an attitude adjusting table provided directly beneath said hoisting and dropping member and movable in a direction which closes said through hole or a direction which opens said through hole, said attitude adjusting table being capable of setting the attitudinal angle of said test subject with respect to said fixing means when in a position in which the through hole is closed, and opening said through hole when the test subject is to be dropped.

4. The fall impact apparatus according to claim 2, further comprising an attitude adjusting table provided directly beneath said hoisting and dropping member and movable in a direction which closes said through hole or a direction which opens said through hole, said attitude adjusting table being capable of setting the attitudinal angle of said test subject with respect to said fixing means when in a position in which the through hole is closed, and opening said through hole when the test subject is to be dropped.

* * * * *